(12) United States Patent
Hince

(10) Patent No.: US 6,617,150 B1
(45) Date of Patent: *Sep. 9, 2003

(54) SOLID-CHEMICAL COMPOSITION FOR BIODEGRADATION COMPRISING PLANT FIBER-CONTAINING MATERIAL AND ENZYMES

(75) Inventor: Eric Christian Hince, Campbell Hall, NY (US)

(73) Assignee: Geovation Technologies, Inc., Florida, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/690,419

(22) Filed: Oct. 17, 2000

Related U.S. Application Data

(63) Continuation-in-part of application No. 09/440,340, filed on Nov. 15, 1999.

(51) Int. Cl.[7] .............................. C12N 1/09; C12N 1/20; B09B 3/00
(52) U.S. Cl. .................. 435/262.5; 435/183; 435/252.1; 435/822
(58) Field of Search .............................. 435/262.5, 183, 435/252.1, 822; 424/93.1

(56) References Cited

U.S. PATENT DOCUMENTS 5,100,455 A * 3/1992 Pinckard et al. .................. 71/9
6,323,007 B1 * 11/2001 Moller et al. .................. 435/74

* cited by examiner

Primary Examiner—David M. Naff
Assistant Examiner—Deborah K. Ware

(57) ABSTRACT

A solid-chemical composition which provides for extraction and absorption of hydrophobic chemical contaminants and further promotes biodegradation of contaminants is provided. The composition comprises one or more plant fiber-containing materials selected from Leguminosae and Phaeophyta in an amount of 20% to 97% by weight percent of the composition, one or more plant fiber-containing materials selected from Gossypium and Cannabacea in an amount of 3% to 80% by weight percent of the composition, and one or more enzymes in an amount of 0.0001% to 3% by weight of the composition. Further, additionally a source of microorganisms capable of producing the enzymes may be contained in the composition. Also disclosed is a method for the bioremediation of the contaminants in environmental media wherein the solid-chemical composition is applied to the environmental media in an amount of about 0.1 gram to 1000 grams of the composition per kilogram of the environmental media.

21 Claims, 2 Drawing Sheets

TOXAPHENE HALF LIVES IN SOIL: Cohorts S7 - S12X

SOLID-CHEMICAL COMPOSITION FOR BIODEGRADATION COMPRISING PLANT FIBER-CONTAINING MATERIAL AND ENZYMES

CROSS-REFERENCE TO RELATED APPLICATIONS

The present application is a Continuation-In-Part of U.S. patent application Ser. No. 09/440,340 filed on Nov. 15, 1999.

BACKGROUND

1. Field of the Invention

This invention discloses the formulation and use of an advanced solid-media chemical composition designed and intended to enhance the removal of petroleum hydrocarbons, halogenated organic contaminants and the oxidized forms of inorganic contaminants from industrial wastes, soils, sediments, sludges, ground waters, surface waters, and the like. In particular, this invention provides an improved means of promoting the anaerobic, biologically mediated degradation, transformation, and/or detoxification of a broad range of organic contaminants in the environment, including, but not limited to, petroleum products such as gasoline, diesel fuel, fuel oils, and lubricating oils; heavy hydrocarbons such as bunker fuels, transformer oils, hydraulic oils, and their constituent polycyclic aromatic hydrocarbons (PAHs); organochlorine pesticides such as DDT and toxaphene; arsenic and/or arsenate-based pesticides; polychlorinated biphenyls (PCBs); dioxins; and halogenated organic solvents such as perchloroethylene, trichloroethylene, trichloroethane, and freon. Either alone or in combination with other liquid and solid-chemical compositions, the present invention also has the potential for the remediation of toxic inorganic contaminants such as cyanide, hexavalent chromium and the oxidized forms of other toxic heavy metals. This invention provides improved means for (i) promoting the solid-phase extraction and absorption of recalcitrant, hydrophobic contaminants from contaminated media, which thereby enhances the bioavailability and biogeochemical reactivity of such contaminants, (ii) creating, enhancing, and maintaining anaerobic conditions which promote biologically mediated denitrification, manganese-reduction, and iron-reduction processes; (iii) promoting reducing conditions favorable to the biologically mediated dehalogenation, transformation, and/or detoxification of halogenated contaminants by naturally occurring microorganisms; (iv) providing a source of complex carbonaceous co-substrates, anaerobic electron acceptors, and nutrients to promote the growth of these contaminant-degrading microorganisms, and (v) providing sources of inoculum of different types of naturally occurring microorganisms which act to directly undertake or indirectly promote the biodegradation, dehalogenation, transformation, and/or detoxification of these contaminants. This invention specifically reveals an improved, primarily organic solid-chemical composition and related methods which are designed to facilitate the aforementioned processes and thereby promote the biodegradation, transformation, and/or detoxification of the aforementioned environmental contaminants.

2. Description of Prior Art

Soil and ground-water pollution caused by chemical contaminants released into the environment is a well documented, world-wide problem. Such chemical contamination is associated with many different types of industrial activities over the last two centuries. Common environmental contaminants include several different types and forms of petroleum hydrocarbons, halogenated organic compounds including solvents (e.g., tetra- and trichloroethene, methylene chloride), pesticides (e.g., DDT and toxaphene), polychlorinated biphenyls (i.e., PCBs), and heavy metals and other inorganic contaminants such as cyanides. The available toxicological data indicates that many of these contaminants, in particular many of the halogenated organic compounds, are either carcinogenic or potentially carcinogenic to both man and animals. In addition, the available environmental and ecological data have shown that many of these contaminants tend to persist in the environment for long time periods and, consequently, they tend to accumulate in the tissues of biological organisms up the food chain. The long-term stability and extremely slow degradation of many such environmental contaminants presents a substantial, long-term hazard to human health and the environment throughout the industrialized world.

Many of the so-called conventional methods for the remediation or clean-up of chemically contaminated wastes, waters, soils, and sediments have generally involved either the physical removal of the contaminated media or the simple mass transfer of the contaminants from one media (e.g., soil) to another (e.g., air). In general, such physical-treatment technologies do not involve the chemically and/or biologically mediated breakdown, transformation, or detoxification of the contaminants. Two of the most common categories of physical environmental remediation technologies are the excavation of contaminated soils and the pumping and subsequent treatment of contaminated ground water. The excavation of contaminated soils is often followed by their disposal in a landfill, which can pose a potential long-term risk to the environment. Many ground-water pump-and-treat processes involve the simple mass-transfer or "stripping" of the contaminants from the water into the air. Another common physical-treatment method involves the use of granular activated carbon (GAC) reactors to treat chemically contaminated waters. When contaminated water is passed through a GAC reactor, the contaminants are physically adsorbed onto the carbon particles, thereby producing another contaminated media which requires subsequent disposal and/or treatment. Each of these physical-treatment technologies share the same disadvantage—i.e., they do not reduce the actual amount or toxicity of the chemical contaminants, but rather they simply move the contamination from one place to another or from one media to another.

Another well-known physical treatment process which involves the thermal treatment or incineration of the contaminated materials can be an effective albeit expensive means of breaking down the molecular structure of the contaminants into non-hazardous products. For example, high-temperature incineration is known to be effective for the treatment of materials containing pesticides and PCBs. Thermal-treatment methods require the use of sophisticated and operation-and-maintenance-intensive equipment, the costs of which are passed on to industry in the form of expensive unit costs for soil treatment. In addition, because thermal-treatment processes are rarely, if ever, one-hundred-percent effective in the destruction of the contaminants, they can produce atmospheric emissions of contaminants or the toxic by-products of contaminants. For example, the incomplete incineration of PCBs can produce dioxins, which in turn are significantly more toxic than their "parent" PCB compounds.

A third category of environmental-remediation treatment technologies, bioremediation, involves the use of microorganisms to convert chemical compounds into innocuous or less harmful chemical compounds. Bioremediation technologies generally have lower costs associated with their use and implementation than do the competing physical technologies. Bioremediation technologies are also more adaptable to different types of contamination problems and variations in field conditions than are physical-treatment technologies.

The most promising bioremediation technologies provide the additional capability of treating contaminated media in-situ, i.e., in place, without the need for ground-water pumping or soil excavation. Current trends in bioremediation technology indicate that the most technically feasible and commercially successful bioremediation technologies are those which utilize indigenous or "native" contaminant-degrading bacteria (CDB), fungi and other microorganisms which are naturally present in the contaminated media. The presence of CDB in many different types of environments has been extensively reported in the scientific literature. There is an extensive body of prior art literature and patents concerning various means of using both aerobic and anaerobic CDB (as well as engineered or cultured bacteria) to biodegrade organic contaminants in water, soil, and industrial wastes. For example, it has been reported that native Alcaligenes spp., Pseudomonas spp., and Enterobacter spp. can degrade a number of pesticides and polychlorinated biphenyls (Nadeau et al., 1994, *Applied and Environmental Microbiology*; Aislabie et al., 1997, *New Zealand Journal of Agricultural Research*; Galli et al., 1992, *Pseudomonas: Molecular Biology and Biotechnology*). Given the significant advantages of using native microorganisms versus the need to introduce cultured or engineered microorganisms, methods which involve the use of artificially introduced microorganisms (e.g., U.S. Pat. No. 5,932,472) are declining in favor within both the scientific and engineering communities. Recent trends in the art and literature acknowledge a growing understanding of the use of anaerobic biological processes in the treatment of many different types of contaminants that are otherwise recalcitrant under aerobic conditions. In particular, trends in the art reflect a growing understanding of the need and importance of achieving and maintaining anaerobic conditions and other factors which favor the biologically mediated reduction, biodegradation, transformation, and/or detoxification of recalcitrant organic and inorganic contaminants in the environment.

The current understanding reflected by the art is that the recalcitrant nature of many halogenated organic contaminants, polynuclear aromatic hydrocarbons (PAHs), other heavy (i.e., high-molecular weight) hydrocarbons, and the like is related to the hydrophobic nature and extremely low solubilities of the contaminants. Consequently, the "bioavailability" of these contaminants, i.e., their availability to biological degradation processes mediated by microorganisms, is extremely limited under most environmental conditions. The prior art describes the use of chemical methods (e.g., Szejtli, et al., U.S. Pat. No. 5,425,881) and thermal methods (e.g., Rothmel, et al., U.S. Pat. No. 5,567,324) to increase bioavailability. For a number of chemically complex hydrophobic chlorinated organic compounds, such as pesticides and PCBs, the prior art has suggested that the higher molecular weight (i.e., more chlorinated) compounds can not be practically biodegraded and thus bioremediation techniques have been all but abandoned with respect to the treatment of such compounds in the environment. For example, through laboratory and pilot-scale experiments directed at the investigation of bioremediation processes on Hudson River sediments contaminated with PCBs, General Electric (GE) researchers determined that the PCBs associated with the sediments consisted of both a labile (i.e., biologically usable) fraction and a resistant (i.e., refractory or relatively non-biologically usable) fraction (General Electric Company, 1992). The labile fraction was described by GE as the lower-molecular weight, less-chlorinated congeners that could be readily desorbed from the sediments. GE described the resistant fraction as the higher-molecular weight congeners that were adsorbed or otherwise bound to the natural organic matrix of the sediments thus greatly limiting their bioavailability to microorganisms. Inoculations with a purified PCB-degrading bacterial strain failed to improve the rate or extent of PCB reduction in the GE experiments.

In contrast to the present invention, further studies along the lines of GE's prior work have all but given up on the biodegradation of the resistant PCB congeners and have instead focused on the potential reduction of the environmental risks posed by these congeners via the long-term biostabilization of these congeners in the sediments (Gan and Berthouex, 1994; Alcock et al., 1995). These studies have further suggested that PCB biodegradation continues to occur slowly over an extended time frame as specific PCB congeners become bioavailable (Gan and Berthouex, 1994; Alcock et al., 1995).

U.S. Pat. No. 5,902,744 to Gray et al. (Stauffer Management Company) teaches the art of composting organic nutrients (e.g., manure, activated sludge) and a bulking material (e.g., alfalfa) to decontaminate toxic cyclical chlorinated aromatic compounds. The method disclosed by Gray et al. also describes the use of cyclical and/or alternating aerobic and anaerobic treatment steps. Gray et al. does not discuss or disclose the art of using the plant material to increase the bioavailability or biogeochemical reactivity of the contaminants or the use of these plant materials to help create or control anaerobic conditions. Gray et al. disclose means by which moist air is moved through the compost and chemical reducing agents, such as sulphite and acetate, are added to maintain anaerobic conditions. Unlike the present invention, Gray et al. does not teach or disclose the importance of legume-related or plant-fiber degrading organisms to bioremediation processes which involve the addition of plant-material or means or methods of enhancing the growth and activity of such organisms to optimize the degradation of contaminants in association with plant material. Gray et al. (U.S. Pat. No. 5,902,744) does not disclose the compositions or methods of the present invention.

Unlike the present invention, U.S. Pat. No. 5,100,455 to Pinckard and Gill, and U.S. Pat. Nos. 5,525,139 and 5,609,668 to Gill disclose the method of achieving specific carbon-to-nitrogen ratios, i.e, within the range of 10:1 to 30:1, as provided for by composting plant material from the families Leguminosae (e.g., alfalfa) and Gossypium (e.g., cotton) at a rate of up to 20% by volume of the contaminated soil. These patents further disclose methods and means for the composting of the plant material and the prior inoculation of such compost (with soil from the chemical spill or with the contaminant(s) of concern) at an off-site location by establishing compost windrows in order to establish populations of the indigenous, presumably contaminant-degrading bacteria. Furthermore, the methods and means described by this prior art are unclear as to whether the contaminated materials must be treated at an off-site location or whether the compost can be applied in-situ. These prior art patents also do not teach or disclose the importance of legume-related and/or fiber-degrading microorganisms to bioremediation processes which involve the addition of plant-material or means or methods of enhancing the growth and activity of such organisms to optimize the degradation of contaminants in association with the plant material. Accordingly, Pinckard and Gill (U.S. Pat. No. 5,100,455) and Gill (U.S. Pat. Nos. 5,525,139 and 5,609,668) do not disclose the present invention.

Burge (*J. Agr. Food Chem.*, 1971) and Guenzi and Beard (*Science*, 1967; *Soil Sci. Soc. Amer.*, 1968) investigated the use of "ground alfalfa" or "alfalfa volatiles" obtained by the distillation of an alfalfa-water slurry to enhance the anaerobic degradation of DDT from soil. Parr and Smith (*Soil Science*, 1976) teach a similar method for the degradation of toxaphene. The results of each of these prior studies indicated that the processes of pesticide dechlorination were both biological and anaerobic in nature. These investigators hypothesized that the addition of the plant material provided energy which in turn increased the rates of contaminant conversion by the microorganisms. None of the prior art described by Burge (*J. Agr. Food Chem.*, 1971), Guenzi and Beard (*Science*, 1967; *Soil Sci. Soc. Amer.*, 1968) and Parr and Smith (*Soil Science*, 1976) disclose the specific chemical compositions or methods for bioremediation of the present invention.

U.S. Pat. No. 6,020,293 to Ahmed et al. (Kay Chemical Company) discloses an enzymatic detergent composition for degrading and removing bacterial cellulose buildup in sugar and/or alcohol enriched drains. The cleaners disclosed by Ahmed et al. contain biologically derived acid cellulase enzymes that directly attack native cellulose, native cellulose derivatives, and soluble cellulose derivatives. Ahmed et al. do not disclose the use of this product for the degradation of plant-derived cellulose nor for the application to media other than impacted drains; hence, Ahmed et al. does not disclose the compositions or methods of the present invention.

U.S. Pat. No. 5,994,121 to Stolzenburg et al. (RMT, Inc.) discloses means and methods for degrading recalcitrant organic contaminants by applying enzymes derived from Pseudomonas sp. into the affected soil or waste which directly degrade the contamination. Stolzenburg et al. does not disclose the importance of increasing the bioavailability and/or biogeochemical reactivity of the contaminants via the absorption or solid-phase extraction of the contaminants from the environmental media. Likewise, this prior art does not disclose the use of enzymes to break down the materials which the contaminants have absorbed within or adhered to, thereby greatly increasing the bioavailability of the contaminants to a broad spectrum of naturally-occurring contaminant-degrading microorganisms. Stolzenburg et al., therefore, do not disclose the use of enzymes for the purposes revealed in the present invention.

U.S. Pat. No. 5,609,667 to Dickerson (Product Services Co.) discloses means and methods for bioremediation, limited to the bioremediation of hydrocarbon-contaminated soils, which incorporate the use of a solid composition comprised primarily of cotton-lint derived cellulose material (and/or other byproducts of cotton and cotton-seed processing) as well as ammonium sulfate. Dickerson (U.S. Pat. No. 5,609,667) was a continuation-in-part of an abandoned patent application, Ser. No. 08/219,843 filed Mar. 30, 1994. Dickerson (U.S. Pat. No. 5,609,667) specifically discloses the superior "wicking" action of his cotton-lint composition relative to other cellulose-based compositions and clay-mineral based compositions with respect to its ability to remove petroleum hydrocarbons from contaminated soils. Dickerson (U.S. Pat. No. 5,609,667) does not disclose the importance of legume-related or fiber-degrading microorganisms to bioremediation processes which involve the addition of fibrous plant materials or means or methods of enhancing the growth and activity of such organisms to optimize the degradation of contaminants which become incorporated into the plant materials. Dickerson (U.S. Pat. No. 5,609,667) does not disclose the compositions or methods of the present invention.

U.S. Pat. Nos. 5,411,664 and 5,618,427 to Seech et al. (W. R. Grace) disclose practically identical methods for the respective biodegradation of halogenated aromatic compounds (US. Pat. No. 5,411,664) and nitroaromatic compounds (U.S. Pat. No. 5,618,427). Both patents disclose the use of both fibrous organic matter and multi-valent metal particles to the contaminated media. These patents discuss adding these amendments to soil, water or sediments and subsequently incubating these media under anaerobic conditions conducive to the growth of the indigenous contaminant-degrading microorganisms. Like Dickerson (U.S. Pat. No. 5,609,667), the patents to Seech et al. disclose that the fibrous nature of the plant materials used is important to enable the organic contaminant to become absorbed into the fibrous structure of the plant material which enhances the extent of contaminant removal from the environmental media. Seech et al. do not disclose the importance of legume-related or fiber-degrading microorganisms to bioremediation processes which involve the addition of fibrous plant materials or means or methods of enhancing the growth and activity of such organisms to optimize the degradation of contaminants which become incorporated into the plant materials. Unlike the present invention, Seech et al. also disclose the use of multi-valent metals, (preferably iron or magnesium), in combination with the fibrous plant matter wherein the multi-valent metals are specifically capable of being both oxidized and reduced back and forth under normal environmental conditions. U.S. Pat. Nos. 5,411,664 and 5,618,427 to Seech et al. (W. R. Grace) do not disclose the chemical compositions or methods taught in the present invention.

U.S. Pat. No. 5,078,899 to Garrison (Idaho Research Foundation, Inc.) discloses a method of treating mine drainage water to remove ferric hydroxide, which is not the subject of the present invention. Although Garrison (U.S. Pat. No. 5,078,899) does not disclose the present invention, the present invention provides for the beneficial use of the wastes produced by the oxidation of mine drainage waters, e.g., ferric oxyhydroxides and the like, as an optional component of the chemical compositions disclosed herein.

SUMMARY OF THE INVENTION

In accordance with the present invention there is provided novel and improved solid-chemical compositions and associated methods and means for the use of these compositions to promote the anaerobic, biologically mediated, degradation, transformation, and/or detoxification of organic contaminants, and potentially certain inorganic contaminants as well, which may be present in solid and liquid wastes, soils, sediments, and water bodies. The principles of this invention provide for the relatively rapid and cost-effective anaerobic, biologically mediated decontamination of such contaminants which are converted into non-hazardous mineral forms and/or less hazardous by-products.

A further object of the invention is to present means by which to overcome the disadvantages associated with not only the traditional methods of remediation previously described but the limitations of other more recent and/or technically advanced methods and means of chemical-reduction based remediation and bioremediation described in the prior art. The present invention has the further advantage that it can be used effectively either ex-situ or in-situ. The preferred embodiments of the present invention offer the further advantages of providing means of promoting the bioremediation of contaminated sediments in-situ beneath bodies of natural water such as oceans, lakes, rivers, streams, and the like, and man-made water bodies such as waste-treatment lagoons and the like. The present invention also provides for significant cost savings relative to other means and methods for environmental remediation, as it can reduce or eliminate the need for excavation, pumpage, transportation, and/or off-site treatment of contaminated wastes, soil, or water.

The present invention is based upon discoveries from recent and ongoing experiments that several inter-related conditions must be achieved and maintained within the matrix of the contaminated media to enable the effective biodegradation of recalcitrant organic contaminants in the environment. Accordingly, the purpose of the present invention is to provide solid-chemical compositions and methods and means for their use which specifically: (1) increase the bioavailability and/or biogeochemical reactivity of the contaminants via the absorption and/or solid-phase extraction of contaminants from environmental media; (2) create and maintain anaerobic if not anoxic conditions by facilitating the biologically mediated removal of the available oxygen from the media; (3) create and maintain reducing conditions (i.e., negative Eh values) and near neutral to slightly acidic pH conditions ($6 \leqq pH \leqq 8$) which favor anaerobic, biologically mediated chemical-reduction reactions, e.g., the reductive dehalogenation of halogenated organic contaminants; and (4) provide means for maintaining conditions (1)–(3) for sufficiently long periods of time to enable the biologically mediated degradation, transformation, and/or detoxification reactions to proceed to the extent that the concentrations and/or toxicity of the contaminants are reduced to acceptable levels.

The discoveries disclosed herein indicate and/or strongly suggest that such contaminants can be effectively degraded, transformed, and/or detoxified by indigenous, contaminant-degrading bacteria when the solid-chemical compositions disclosed herein are applied to the contaminated media and the media are subsequently maintained under conditions favorable to the anaerobic microorganisms and the biogeochemical reactions mediated by these organisms, i.e., the media are kept moist or nearly saturated with water. Through a number of experiments conducted by the inventors, it has been further discovered that the primarily organic solid-chemical compositions disclosed herein are capable of supporting the growth of indigenous bacterial populations which include both legume-related microorganisms such as Rhizobium spp. and Bradyrhizobium spp. and the like and fiber-degrading (i.e., lignin- and cellulose-degrading) bacteria such as Fibrobacter spp. and the like. In addition, the present invention includes plant-fiber and organic-substrate degrading enzymes such as cellulases, amylases, glucanases, hemi-cellulases, proteases, and lipases. For purposes of explanation and not limitation, it is believed that the aforementioned legume-related microorganisms and plant-fiber and organic substrate degrading microorganisms and enzymes greatly enhance the anaerobic biodegradation, transformation, and/or detoxification of recalcitrant contaminants either directly and/or by breaking down the cellulose-containing materials which the contaminants have absorbed within and/or adhered to, thereby greatly increasing the bioavailability of the contaminants to a broad spectrum of other microorganisms. These and other objects and advantages of the present invention will become apparent to those skilled in the art following the detailed description of the invention which reveals the novel combination of solid chemical compositions described herein, and more particularly as defined by the appended claims.

BRIEF DESCRIPTION OF THE FIGURES

Embodiments of the present invention will now be described more fully with reference to the following drawings in which.

DETAILED DESCRIPTION OF THE INVENTION

Figure 1:
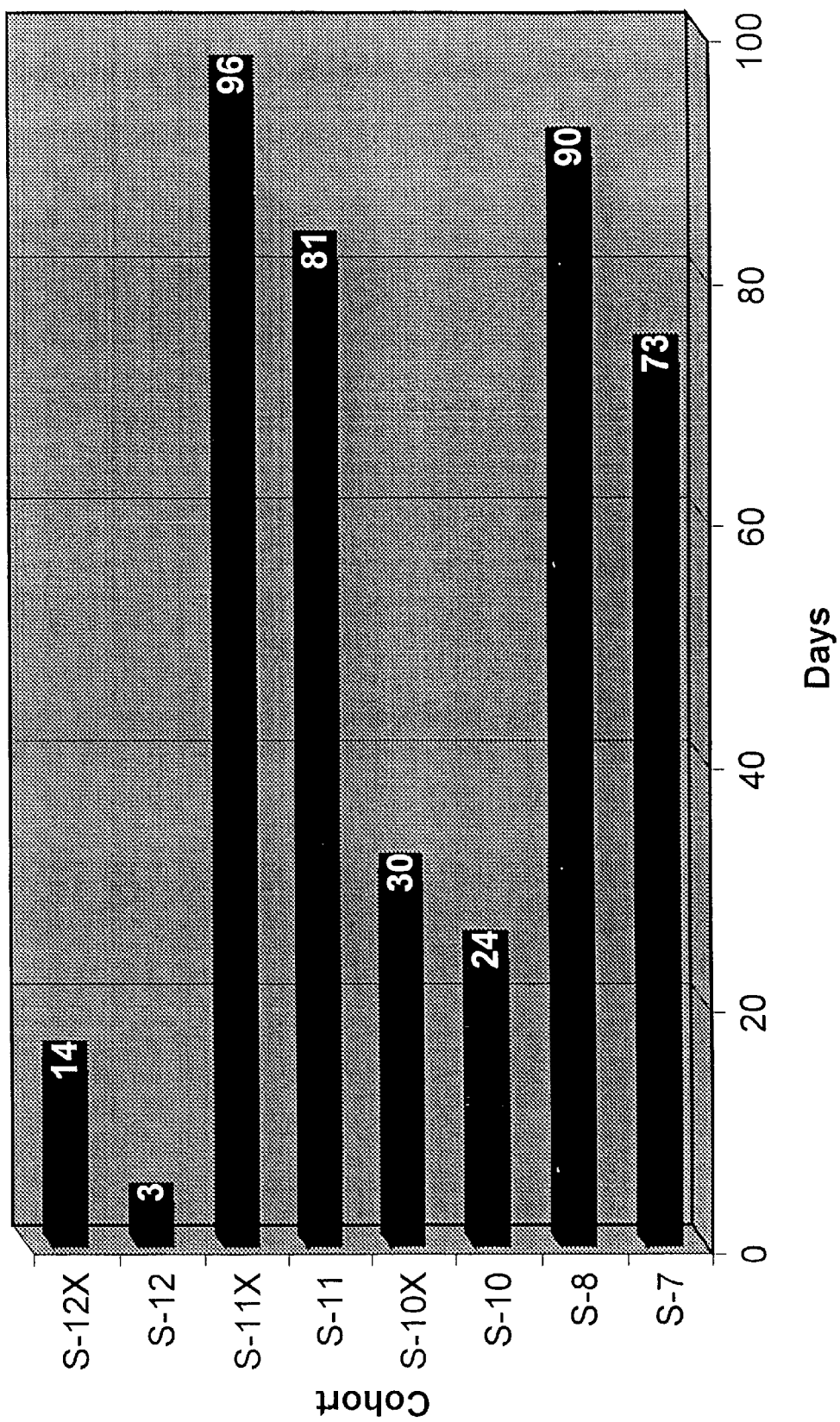
FIG. 1 shows the effect of several simplified embodiments of the disclosed solid-chemical compositions in combination with a previously disclosed liquid-chemical composition (Hince et al., U.S. Pat. No. 6,020,185) on DDT biodegradation rates.

The present invention disclosed herein provides unique solid-chemical compositions and methods for the bioremediation of wastes and environmental media contaminated with organic contaminants such as petroleum hydrocarbons (e.g., gasoline, oils, and PAHs); halogenated solvents such as tetrachloroethene, trichloroethene, 1,1,1-trichloroethane, freon, and the like; and other recalcitrant halogenated organic compounds such as DDT, toxaphene, PCBs, dioxins, and the like. In addition, the compositions disclosed herein are believed to be capable of promoting the biologically mediated transformation and/or detoxification of certain inorganic contaminants such as arsenic-based pesticides, cyanides, hexavalent chromium, the oxidized forms of other toxic transition metals, and the like when used either alone or in combination with other liquid and/or solid chemical compositions.

In the practice of the present invention, the disclosed solid-chemical compositions would first be prepared by mixing their components together prior to their use at a contaminated site. Next, the disclosed solid-chemical compositions are applied to, and ideally, mixed into the contaminated wastes (e.g., sludges, solid and/or liquid wastes, and the like) or other contaminated media such as soils, sediments, or water bodies, and the like. The use as intended of the disclosed solid-chemical compositions and methods provide for a combination of means, mechanisms, processes, and factors which enhance the anaerobic biodegradation, transformation, and/or detoxification of recalcitrant environmental contaminants including:

(1) The plant-derived components in the disclosed solid-chemical compositions promote anaerobic and reducing conditions and the physical and biogeochemical extraction of the hydrophobic substances from the contaminated media and into the matrix of the plant fibers, thereby greatly increasing the bioavailability and biogeochemical reactivity of the contaminants to a broad spectrum of contaminant-degrading microorganisms.

(2) The solid-chemical compositions disclosed herein provide a combined source of organic inoculum and substrates for soil, legume-related and fiber-degrading microorganisms such as Pseudomonas spp., Rhizobium spp., Bradyrhizobium spp., Fibrobacter spp., Clostridium spp. and the like. In addition, the composition provides a source of plant-fiber and organic-substrate degrading enzymes such as cellulases, amylases, glucanases, hemi-cellulases, proteases, and lipases. For purposes of explanation and not limitation, it is believed that the legume-related microorganisms and fiber-degrading enzymes and microorganisms greatly enhance the anaerobic biodegradation, transformation, and/or detoxification of recalcitrant contaminants either directly and/or by breaking down the plant-fiber materials which in turn make the contaminants which have become adhered to and/or impregnated therein available to a broad spectrum of anaerobic microorganisms. This latter advantage of the present invention represents a major and extremely important advancement in the art. Hence, the solid-chemical compositions disclosed herein provide unique advantages which greatly enhance the speed and effectiveness of the anaerobic, biologically mediated biodegradation, transformation and/or detoxification of recalcitrant contaminants.

(3) The organic materials derived from nitrogen-fixing plants included in the solid-chemical compositions disclosed herein provide a combination of carbonaceous co-substrates; nitrogen-based electron acceptors such as nitrates and nitrites; complex nutrient forms of nitrogen such as amines, proteins, and enzymes; fatty acids; and complex nutrient forms of phosphorus such as phospholipids for anaerobic soil, legume-related and fiber-degrading microorganisms as well as for other anaerobic microorganisms capable of denitrification processes. Hence, the use of these nitrogen-fixing and/or leguminous plant materials as disclosed in the present invention provides for ideal growth conditions of said microorganisms. In addition, the nitrogenous electron acceptors and nutrients provided by these materials provide a means by which to promote the anaerobic biodegradation of the other organic components of the disclosed chemical compositions, as well as the contaminants incorporated therein, by organisms capable of denitrification, metal-reduction and other anaerobic respiration processes.

(4) In addition to the foregoing, and for purposes of explanation and not limitation, the biogeochemically produced (i.e., 'biogenic') ferric oxyhydroxides which may be included in the solid-chemical compositions disclosed herein are believed to provide a unique and important source of inoculum for metal-reducing bacteria such as Geobacter spp., Thiobacillus spp. and the like. Trends in the recent literature indicate or otherwise suggest that such metal-reducing microorganisms play an important role in the "natural" biodegradation, transformation and/or detoxification of many contaminants in the environment. Hence, inclusion of the biogeochemically produced ferric oxides, hydroxides, and oxyhydroxides in the present invention provides a unique and improved means of enhancing the activity of such microorganisms.

Based on the foregoing and in accordance with the present invention, there are provided means for the enhanced anaerobic microbial degradation, transformation, and/or detoxification of recalcitrant organic and inorganic chemical contaminants in wastes, soils, and sediments, and comprising the formulation, processing and use of unique solid-chemical compositions. The primarily organic solid-chemical composition disclosed herein is comprised of from four-to-nine components.

In the preferred embodiment of the present invention, the first component of the disclosed composition is comprised of materials derived from nitrogen-fixing plants-selected from the plant families Leguminosae (e.g., Lespedeza spp., Glycine spp., Medicago ssp., Vicia spp., Lathyrus spp., Trifolium spp and the like) and Phaeophyta (e.g., Sargassum spp.). The second essential component of the disclosed composition comprises materials selected from the plant families Gossypium (e.g., cotton) and Cannabacea (e.g., hops and hemp). Another organic component of the disclosed composition is selected from the group comprising inoculum for soil, legume-related, fiber-degrading, or metal-reducing bacteria such as Pseudomonas spp., Rhizobium spp., Bradyrhizobium spp., Fibrobacter spp., Clostridium spp., Geobacter spp. and the like. The fourth organic component of the present invention is selected from the group comprising plant-fiber and organic-substrate degrading enzymes such as cellulases, amylases, glucanases, hemi-cellulases, proteases, and lipases and/or biologically active material containing aerobic and anaerobic microorganisms which produce such enzymes. A final optional plant-derived component of the disclosed composition comprises materials derived from the plant families Triticum and Aegilops (e.g., wheat, oats and the like). The remaining inorganic components of the disclosed composition would be selected from the groups comprising nitrate salts, ringed metaphosphates and/or linear polyphosphates, and chelating and/or acidifying agents.

In the preferred embodiment of the present invention, the first plant-derived component (a) of the disclosed chemical composition constitutes from 10% to 97% of the total composition by weight and is comprised of (i) the fine-particulate, dehydrated, dried and/or processed forms of nitrogen-fixing plant materials selected from the plant families Leguminosae and Phaeophyta and/or (ii) agriculturally cultivated plant materials selected from the plant family Leguminosae. In the preferred embodiment of the present invention in which leguminous materials are used in component (a) of the disclosed composition, such materials would preferably be selected from the group comprising Lespedeza spp., Medicago ssp. (e.g., alfalfa), Vicia spp. (e.g., vetch), Glycine spp. (e.g., soy), Lathyrus spp. (e.g., indian vetch), Trifolium spp. (e.g., clovers) and the like. In the preferred embodiment of the present invention in which materials from the plant family Phaeophyta are used in component (a) of the disclosed composition, such materials would preferably be selected from the group comprising Sargassum spp. In the preferred embodiment of the present invention which incorporates the use of the dehydrated, dried and/or similarly processed forms of said nitrogen-fixing plant materials, the said materials are further selected from the group comprising flours, powders, dusts, meals, mids, husks, hulls, hays, straws, pellets, and/or other commercially available forms of these materials.

In the preferred embodiment of the present invention, the second plant-derived component (b) of the disclosed chemical composition constitutes 3% to 80% of the total composition by weight and would be comprised of (i) the industrially processed and/or (ii) agriculturally cultivated plant materials selected from the families Gossypium (e.g., cotton) and Cannabacea (e.g., hops and hemp). The advantages provided for by the use of plant materials selected from the families Gossypium and Cannabacea is that the physical-extraction, absorption, and adsorption of hydrophobic contaminants is enhanced by the fibrous microstructure of such plant materials as well as by the naturally occurring hydrophobic oils and resins present therein. A further distinction of the preferred embodiment of the present invention would include the beneficial use of highly absorbent cotton-containing waste materials such as cotton lint, cotton-mill processing 'dust,' and the like. A distinction of the preferred embodiment of the present invention which includes the use of plant materials selected from the family Cannabacea (e.g., hops and hemp) is that in addition to the fibrous nature of such materials, they contain abundant amounts of relatively insoluble oils and resins which should greatly enhance the ability of these materials to physically and/or biogeochemically extract hydrophobic contaminants from contaminated media. Additional advantages of the preferred embodiment of the present invention which includes the use of hemp and/or hops materials from the plant family Cannabacea would be the relatively low costs and negligible environmental impacts associated with the production of these plant materials, i.e., relative to other agricultural products.

In the preferred embodiment of the present invention, a microbial component (c) is included in the chemical composition of the present invention which constitutes 0.0001% to 3% of the total chemical composition by weight and is comprised of the dehydrated and/or freeze-dried forms of inoculum selected from one or more of the group comprising soil microorganisms (e.g., Pseudomonas spp.), legume-related microorganisms (e.g., Rhizobium spp., Bradyrhizobium spp.), plant-fiber degrading (i.e., lignin- and cellulose-degrading) microorganisms (e.g., Fibrobacter spp., Clostridium spp., and various species of fungi), metal-reducing microorganisms (e.g., Geobacter spp.), and aerobic and anaerobic microorganisms which produce plant fiber and organic substrate degrading enzymes (e.g., Arthrobacter spp., Nocardia spp., Bacillus spp., Aspergillus spp., Trichoderma spp.). In the preferred embodiment of the present invention, particular emphasis is placed on the use of inoculum for plant-fiber degrading microorganisms such as the anaerobic bacteria Fibrobacter spp., Clostridium spp., and the like and/or plant-fiber degrading species of fungi, as well as microorganisms which produce plant fiber and organic substrate degrading enzymes such as Arthrobacter spp., Nocardia spp., Bacillus spp., Aspergillus spp., and Trichoderma spp. A further distinction of the preferred embodiment of the present invention would include the use of "biogenic" ferric oxyhydroxides, such as the type referred to as "yellow boy" which is associated with mine drainage and/or the treatment by-products thereof. For purposes of clarification and not limitation, results of the novel research associated with the present invention suggests that in addition to providing a source of electrons and ferric-iron electron acceptors for metal-reducing bacteria, such biogeochemically produced ferric oxyhydroxides also serve as inoculum for metal-reducing and oxidizing bacteria such as Geobacter spp., Thiobacillus spp., and the like. In summation, component (f) of the disclosed composition provides the advantage of ensuring for an adequate population of the important types of microorganisms in relatively challenging, difficult or otherwise unusual remediation applications of the present invention such as the bioremediation of industrial or hazardous wastes, waste lagoons, natural bodies of water (e.g., oceans, rivers, lakes, streams, and the like), or deep sediments or rock formations where such microorganisms may not be sufficiently abundant.

In the preferred embodiment of the present invention, an additional organic component (d) would be included in the chemical composition which constitutes 0.0001% to 3% of the total chemical composition by weight and is comprised of fiber-degrading enzymes such as cellulases, amylases, glucanases, hemi-cellulases, proteases, and lipases. It is believed that organic component (d) of the disclosed composition greatly enhance the anaerobic biodegradation, transformation and/or detoxification of the contaminants by breaking down the plant-fiber materials which in turn make the contaminants which have become adhered to and/or impregnated therein available to a broad spectrum of anaerobic microorganisms.

For purposes of explanation and not limitation, it is believed that the plant-derived materials included within the chemical composition of the present invention have the capacity to physically and/or biogeochemically extract, absorb, and adsorb hydrophobic organic contaminants from contaminated media. In addition, the plant materials included in the disclosed composition serve as both a substrate and inoculum for legume-related bacteria such as Rhizobium spp., Bradyrhizobium spp., and the like, and plant-fiber degrading microorganisms such as Fibrobacter spp., Clostridium spp., plant-degrading fungi, and the like. Hence, after the contaminants are absorbed within the plant material, they subsequently become "bioavailable" to a broad spectrum of anaerobic microorganisms via the activity of the fiber-degrading microorganisms, microorganisms which produce plant fiber and organic substrate degrading enzymes (e.g., Arthrobacter spp., Nocardia spp., Bacillus spp., Aspergillus spp., Trichoderma spp.), and fiber-degrading enzymes (e.g., cellulases, amylases, glucanases, hemi-cellulases, proteases, lipases). It is further believed the complex enzymatic capabilities of the aforementioned fiber-degrading microorganisms may enable these microorganisms to either degrade the contaminants directly, e.g., through the use of cellulosomes or similar means, or as a co-metabolic function of the degradation of the plant-derived materials included in the chemical composition.

In the preferred embodiment of the present invention, the first inorganic component (e) of the disclosed solid-chemical composition constitutes 0.5% to 30% of the total composition by weight and is selected from the group comprised of sodium nitrate, sodium-potassium, nitrate, potassium nitrate and ferric nitrate. Inorganic component (e) provides both a source of electron acceptors for denitrifying bacteria and other anaerobic microorganisms capable of denitrification and an ammonium-free source of nitrates as the sole inorganic form of nutrient nitrogen in the disclosed solid-chemical composition.

In the preferred embodiment of the present invention, the second inorganic component (f) of the disclosed solid-chemical composition constitutes 0.25% to 15% of the total composition by weight and is preferably selected from one or more of the group comprising ringed metaphosphates and/or linear polyphosphates. Inorganic component (f) of the disclosed composition provides a source of complex, hydrolyzable phosphates as nutrient forms of phosphorus for microorganisms. The provision of complex metaphosphates and/or polyphosphates provides nutrient phosphorus in forms which are relatively non-reactive geochemically and hence more effectively and efficiently utilized by microorganisms. In addition, these complex phosphates also serve as surfactants which enhance the biogeochemical reactivity and bioavailability of organic contaminants.

The third inorganic or non-plant-derived component (g) of the disclosed solid-chemical composition constitutes from 0.01% to 5% of the total composition by weight and is selected from one or more of the group comprising citric acid, humic acid, fulvic acid, sodium citrate and EDTA. Component (g) of the disclosed composition provides a source of both chelating agents and acidifying agents which help promote anaerobic, biologically mediated metal-reduction processes and other biogeochemical processes which are catalyzed by metals. In the preferred embodiment of the present invention, citric acid is used as some or all of component (g) given that it is not only an effective chelator and pH-reducing (i.e., acidifying) agent, but it is a weak organic acid which can help promote microbial processes. The use of humic and/or fulvic acid in component (g) provides similar and complimentary benefits to the use of citric acid.

In the preferred embodiment of the present invention, an additional plant-derived component (h) would be included in the chemical composition which constitutes 0.5% to 30% of the total chemical composition by weight and is comprised of industrially processed or agriculturally cultivated plant materials from the families Triticum and Aegilops (e.g., wheat, oats, and the like). In the preferred embodiment of the present invention, component (h) of the disclosed composition would include the fine particulate, dehydrated or dried forms of agriculturally produced materials or wastes which contain wheat, oats, and the like, e.g., pellets, powders, flours, dusts, meals, mids, husks, hulls, straws, or hays. Plant-derived component (h) of the disclosed composition not only provides an additional capacity to physically extract, absorb, or adsorb hydrophobic contaminants, but provides an additional and complimentary source of organic nutrients and carbonaceous co-substrates including complex sugars, starches, cellulose, and lignin. Hence, component (h) of the disclosed composition is believed to enhance the long-term effectiveness of the use of the disclosed composition.

For purposes of explanation and not limitation, the benefits of the use of nitrogen-fixing plant materials in the disclosed composition, such as the aforementioned leguminous materials, includes the ability of such materials to promote the growth and activity of anaerobic microorganisms which are specifically capable of denitrification-processes which utilize the nitrogenous electron acceptors and nutrients present in these materials. In addition, by providing such nitrogen-fixing plant materials in the amounts of at least 20% of the total composition by weight, these materials provide "excess" amounts of electron acceptors, nutrient forms of nitrogen and phosphorus, proteins, enzymes, and inoculum for plant-fiber degrading microorganisms which promote the biodegradation of the other plant-derived components of the composition as well as the contaminants incorporated therein. Hence, the intended benefits of the use of such nitrogen-fixing plant materials in the disclosed composition provides significant advantages relative to other compositions, methods, and means for bioremediation disclosed in the prior art.

For purposes of explanation and not limitation, it is believed that the fine particulate and dehydrated and/or dried forms of the plant-derived components of the disclosed composition greatly enhance the ability of these materials to physically and/or biogeochemically extract or absorb hydrophobic contaminants relative to other forms of said materials as a direct result of their low water content. It is further believed that the freezing and/or freeze-drying of the plant-derived components of the disclosed composition not only enhances the ability of these materials to physically and/or biogeochemically extract or absorb hydrophobic contaminants relative to other forms of these materials, but increases the relative rates of biodegradation of both the plant materials and the contaminants absorbed within and/or adhered to these materials.

In the preferred embodiment of the present invention in which leguminous materials are included in the first component (a) of the disclosed composition, the leguminous materials can either be applied to contaminated media directly in the form of the fine-particulate and/or industrially processed forms of pellets, meals, husks, hulls, hays, or straws or they can be agriculturally cultivated in-situ by direct plantings of legume seeds or plants in the contaminated soils. The application of the leguminous materials can be conducted before, during or after the application of the other components of the disclosed chemical composition. In the form of the present invention whereby the leguminous materials are agriculturally cultivated in-situ, the preferred embodiment of the invention would include the repeated cutting and mulching of the leguminous plant materials in-situ to both increase the yield (i.e., amount) and to decrease the particle size of the leguminous materials in order to enhance their incorporation into the contaminated soils.

A further aspect of the preferred embodiment of the present invention involving the agricultural cultivation of the leguminous plant materials would involve the overwintering of said materials which is believed to enhance the physical and biogeochemical extraction of the hydrophobic contaminants and their biodegradation via the decay of the leguminous materials in-situ during the dormant, i.e., winter, season. For purposes of explanation and not limitation, the aforementioned "overwintering" of the leguminous materials at sites in which freezing conditions are experienced over the course of a year is believed to greatly enhance the aforementioned advantages of the preferred embodiment of the present invention by "freezedrying" and/or freeze-fracturing of these materials, which consequently helps to distribute the leguminous materials throughout the soil matrix, enhances the ability of these materials to physically and/or biogeochemically extract and/or absorb hydrophobic contaminants and increases the relative biodegradation rates of both the leguminous materials and the contaminants. The overwintering process also promotes the anaerobic bioremediation of contaminants by increasing the bioavailability of the legume-related co-substrates, electron donors and acceptors, nutrients and the like to many different types of microorganisms within the soil matrix.

In the practice of the present invention, the solid-chemical composition of the present invention may be applied to the contaminated wastes or environmental media at rates which are typically in the range of 0.1-to-150 g per Kg of waste, soil, sediment, water or other contaminated environmental media. In general, it is desirable to apply the disclosed composition at a rate in which the mass (or concentration) of the composition is more than a factor of ten greater than the mass (or concentration) of the contaminants of concern within media such as soils, sediments, aqueous sludges and the like. In applications whereby the composition is applied directly to contaminated waste liquids or sludges which contain little to no water, e.g., waste solvents, transformer oils, and the like, it may be necessary to increase the application dose rate to 1 g to 1000 g of the composition per Kg of said wastes.

The chemical composition of the present invention disclosed herein can be applied to contaminated media either ex-situ or in-situ to enhance the bioavailability and/or reactivity of recalcitrant organic and inorganic contaminants and to promote the anaerobic biodegradation, transformation, and/or detoxification of these contaminants. In addition, the preferred embodiments of the present invention allow for the chemical composition disclosed herein to be combined and/or processed into such forms that can easily be applied to the contaminated environment in-situ, eliminating the need to excavate the materials and treat in an ex-situ manner. In particular, another aspect of the preferred embodiment of the present invention is the means and/or methods by which the chemical composition disclosed herein is processed into the forms of pellets, capsules, or tablets, which are easier and safer to store, handle and use than other forms of the disclosed chemical composition. The preferred embodiment of the present invention in the form of manufactured pellets, capsules, and/or tablets is similar in form to those manufactured for the animal feed and pellet-fuel industries, such that this form of the present invention can be readily produced by existing and economical means. The preferred pellet, capsule, and/or tablet forms of the disclosed composition are easier and safer to store, handle, and use than other forms of both the disclosed composition, as well as other compositions, means, and methods for bioremediation disclosed in the prior art.

Another aspect of the preferred pellet, capsule, or tablet forms of the solid chemical composition disclosed herein is that the final specific gravity (i.e., density) of the pellets can easily be adjusted so as to be greater than that of water, such that the pellets readily sink in water. In addition, the pellet, capsule, or tablet forms of the composition disclosed herein provide for the delayed, time-release type of interaction between the composition and the contaminated media—consequently these forms provide for the prolonged release of the various amendments incorporated into the composition. Hence, the pellet, capsule, or tablet forms of the disclosed chemical composition would provide the means by which to utilize the composition in more complicated applications, such as in the bioremediation of contaminated sediments in-situ beneath natural waters (e.g., oceans, lakes, rivers, streams, and the like) and man-made water bodies (e.g., waste-treatment lagoons and the like).

In the practice of the present invention, after the disclosed solid-chemical composition has been applied to the contaminated media, the media would ideally be maintained under conditions favorable for anaerobic microbial growth, i.e., at a moisture content preferably close to 100% of the saturation point or water-holding capacity of the soil or sediment, after the introduction of said chemical composition. In addition, the solid chemical composition-disclosed herein may be supplemented with the use of liquid-chemical compositions which contain one or more components selected from the group comprising nitrates, nitrites, phosphates, surfactants, alcohols, ketones, vegetable oils, mineral oils, corn syrup, barley malt extract, molasses, humic acids, fulvic acids, and chelating agents. Subsequent additions of water and/or liquid chemical compositions can be applied as needed, and may be desirable, in order to promote more rapid and effective contaminant biodegradation.

As described above, the solid chemical-compositions of the present invention disclosed herein provide for unique advantages, means, and methods of achieving the relatively rapid and effective anaerobic bioremediation recalcitrant organic and inorganic contaminants present in wastes, soils, waters, or sediments versus the means and methods disclosed in the prior art. The solid-chemical compositions disclosed herein and the means and methods for their intended use overcome many of the disadvantages associated with traditional remediation methods by providing for the efficient and cost-effective remediation of environmental contaminants on a commercial scale with minimal disturbance to the contaminated area. The solid-chemical compositions disclosed herein and the means and methods for their intended use also overcome many of the disadvantages associated with the more advanced means and methods for the chemical and biological remediation of environmental contaminants disclosed in the prior art.

EXAMPLES

The following examples are provided to illustrate the technical basis, merits and unique advantages provided by the present invention with respect to the treatment of soils contaminated with some of the most extremely recalcitrant contaminants, including the organo-chlorine pesticides DDT and toxaphene, PCBs, and PAHs. These examples are not to be construed as limiting the present invention in any way, but are merely presented as examples of the unique advantages and non-obvious improvements of the present invention over the prior art and to illustrate the practice of the present invention as described in the appended claims.

Example 1

Prior to the development of the present invention, a pilot-scale test of four different approaches to the anaerobic bioremediation of the recalcitrant, hydrophobic organo-chlorine pesticides DDT and toxaphene was conducted from April 1996 though April 1997 in order to investigate the combination of different approaches to the implementation of denitrification-based bioremediation and phytoremediation. One trial, initiated in February 1997 and completed in April 1997, involved the use of an embodiment of a previously disclosed "denitrification-based bioremediation" liquid-chemical composition (Hince et al., U.S. Pat. No. 6,020,185). Among other inventions, Hince et al. disclose several liquid-chemical compositions for promoting anaerobic biodegradation of toxic organic and inorganic compounds under anaerobic conditions including denitrifying, manganese-reducing, iron-reducing, and sulfate-reducing conditions.

The pilot study trial which utilized the liquid-chemical composition previously disclosed by Hince et al. was the most effective method tested for the biodegradation of the pesticides DDT and toxaphene, with significant reductions realized over the course of only three months. However, the recent re-analysis of the data from this pilot study, based largely on the knowledge gained from recent experiments, suggests that the planting of the legume *Lespedeza sericia* in adjacent areas might have significantly contributed to the observed reductions in pesticide concentrations. In comparison to the optimal test plot, the plots planted with the *Lespedeza sericia* also realized reductions in the pesticide concentrations, albeit over a longer period (i.e., one year). Regardless of the fact that upwards of 98–99% reductions of DDT and toxaphene levels were achieved in the most successful test plots of the 1996–1997 study, the underlying mechanisms and factors responsible for these results were either not well understood or had not yet been identified at that time.

Subsequent to the completion of the initial pilot-scale test, microcosm studies were conducted at a research institution without the use of the solid-chemical composition disclosed herein in an attempt to optimize the formulation and application of the liquid-chemical compositions previously disclosed by Hince et al. As these microcosm studies focused on the optimization of these previously disclosed liquid-chemical compositions, no organic or inorganic compositions, such as plant-derived materials or geochemical amendments, were used in these experiments. These microcosm studies were unable to reproduce the results achieved in the initial pilot study. Nonetheless, the data from these experiments led to further research concerning other means and methods of enhancing the anaerobic biodegradation of the pesticides DDT and toxaphene.

A second pilot-scale test of four different approaches to the anaerobic bioremediation of the pesticides DDT and toxaphene was conducted from December 1998 through June 1999 in order to investigate the use of liquid-chemical compositions previously disclosed by Hince et al. in combination with various inorganic, i.e., geochemical compositions. The second pilot-scale test was also not very successful in reducing organochlorine pesticide concentrations. The relative lack of success of the studies conducted after the 1996–1997 pilot study, as well as the information described in EXAMPLE 2 below, led the inventors to conduct additional experiments to investigate the effects of various organic and inorganic chemical compositions and combinations thereof on pesticide degradation.

Example 2

An investigation was undertaken in the late fall of 1999 to identify the types of bacteria present in uncontaminated, pesticide contaminated (but untreated) and post-treated soils associated with the pilot studies described in EXAMPLE 1. Soil samples representative of these conditions were analyzed using denaturing gradient gel electrophoresis (DGGE) methods to separate and sequence the 16S rDNA genes of the bacteria present. The results of the DGGE 16S rDNA analyses were compared to an international computer database for bacterial DNA. The resultant DGGE "gels" revealed that novel Fibrobacter spp. dominated the microbial community present in the post-treated sample, whereas such species were significantly less abundant in the DGGE gels for the contaminated-but-untreated sample and the "clean" sample. The results also indicated that other novel and/or previously unexpected "adapted" populations of soil and/or legume-related bacteria such as Rhizobium spp. and Bradyrhizobium spp., as well as soil bacteria such as Pseudomonas spp. and Geobacter spp., were evident in the bacterial communities identified in the samples from the contaminated and/or successfully treated locations.

Subsequent investigation of the scientific literature and related research conducted from December 1998 to date has indicated that Fibrobacter spp. are known to be plant-fiber degrading (e.g., lignin- and cellulose-degrading) bacteria for which the "conventional wisdom" and prior art have held are most commonly associated with the breakdown of plant fiber in the rumen of cattle and similar environments. Furthermore, the available literature indicate that Fibrobacter spp. are anaerobic bacteria which degrade cellulose and lignin using a fermentative-type metabolism. In addition, the subsequent research has indicated that the Rhizobium spp. and Bradyrhizobium spp. are legume-related bacteria associated with the roots of legumes which are responsible for the anaerobic fixation of elemental nitrogen. Moreover, Bradyrhizobium spp. were found to be the specific bacterial symbionts found in association with the roots of Lespedeza spp. Hence, these results led to the novel hypothesis disclosed herein that such fiber-degrading bacteria, (and possibly the legume-related bacteria as well), were either directly responsible for the biodegradation of the pesticides and/or carried out processes which greatly increased the bioavailability of the pesticides to other anaerobic, contaminant-degrading microorganisms.

Example 3

Several additional sets of bench-scale, microcosm experiments were conducted in the laboratory to investigate the effectiveness of using different embodiments of the primarily organic solid-chemical composition of the present invention disclosed herein alone or in combination with either a previously disclosed liquid-chemical composition (Hince et al., U.S. Pat. No. 6,020,185), a novel liquid-chemical composition, and/or a geochemical (i.e., inorganic) solid-chemical composition.

Figure 2:
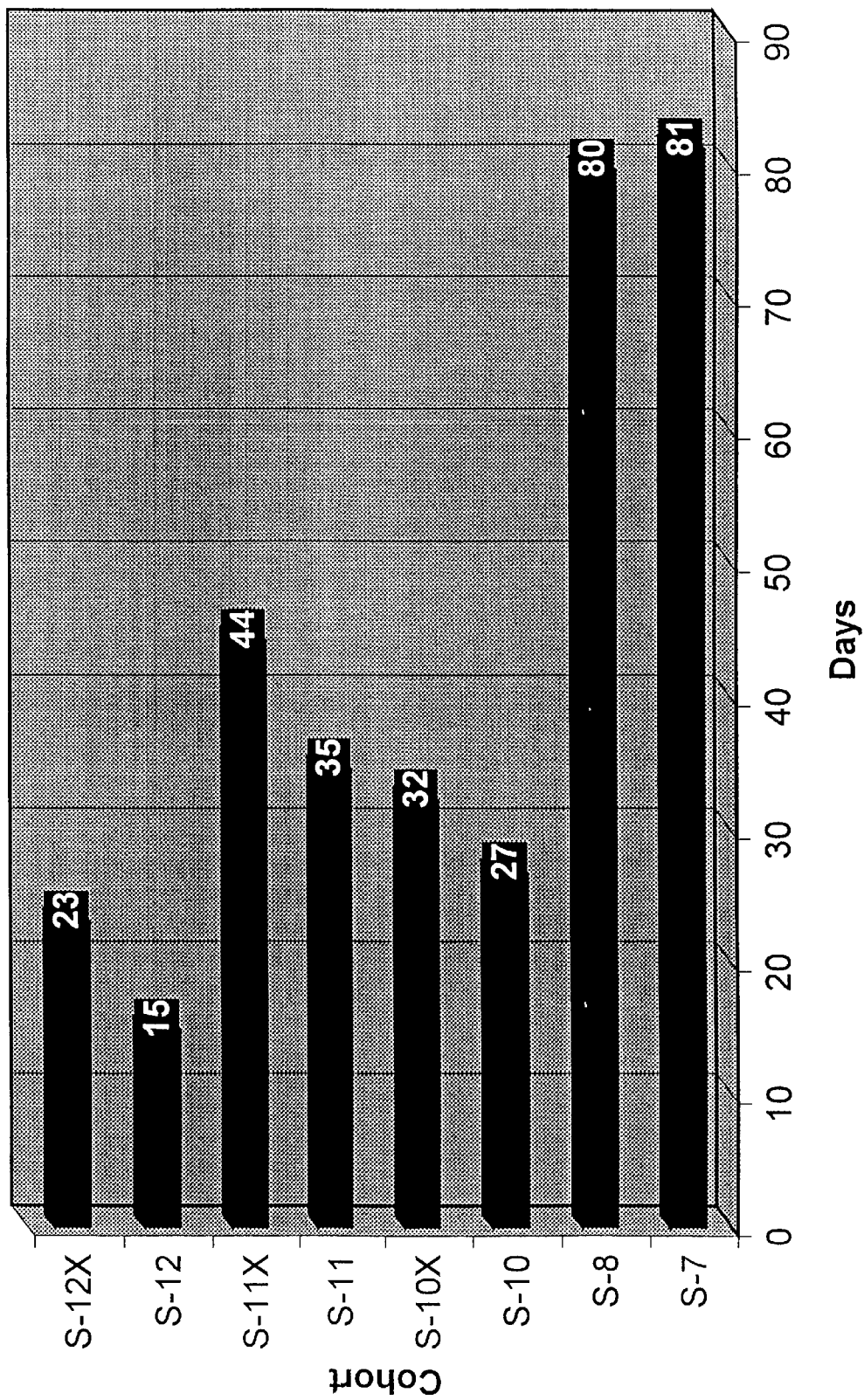
FIG. 2 shows the effect of several different embodiments of the disclosed solid-chemical composition in combination with a previously disclosed liquid-chemical composition (Hince et al., U.S. Pat. No. 6,020,185) on toxaphene biodegradation rates.

As shown in FIGS. 1 and 2, experimental cohorts S-7 and S-8, which were only treated with an inorganic solid-chemical composition or a liquid-chemical composition previously disclosed by Hince et al. demonstrated pesticide biodegradation half-lives on the order of a minimum of three months. Cohorts S-10X, S-11X, and S-12X, which were treated with a simplified embodiment of the primarily organic solid-chemical composition disclosed herein and a previously disclosed liquid-chemical composition (Hince et al.), achieved better treatment half-times which ranged from 17-to-99 days for DDT and 28-to-36 days for toxaphene.

The invention has been described with reference to particular embodiments. However, it should be obvious to those skilled in the art to which this invention pertains that other modifications and enhancements can be made without departing from the scope of the claims that follow.

I claim:

1. A solid-chemical composition which provides for extraction and absorption of hydrophobic chemical contaminants and further promotes biodegradation of said contaminants comprising:

a. One or more plant fiber-containing materials from plant families selected from the group consisting of Leguminosae and Phaeophyta, comprising from about 20% to 97% by weight percent of the composition;

b. One or more plant fiber-containing materials from plant families selected from the group consisting of Gossypium and Cannabacea, comprising from about 3% to 80% by weight percent of the composition; and c. One or more enzymes selected from the group consisting of plant-fiber degrading enzymes and organic-substrate degrading enzymes, comprising from about 0.0001% to 3% by weight percent of the composition.

2. A chemical composition in accordance with claim 1, wherein said plant-fiber degrading enzymes and organic-substrate degrading enzymes are selected from the group consisting of cellulases, amylases, glucanases, hemicellulases, proteases, chitinases, lipases and combinations thereof.

3. A chemical composition in accordance with claim 1, further comprising a source of microorganisms which produce plant-fiber and organic-substrate degrading enzymes, from about 0.01% to 3% by weight percent of the composition.

4. A chemical composition in accordance with claim 3, wherein said source of microorganisms is comprised of forms selected from the group consisting of dehydrated cultures, freeze-dried cultures, encapsulated cultures, spores and combinations thereof.

5. A chemical composition in accordance with claim 1, which further includes an inorganic source of microbial electron acceptors and an ammonium-free source of inorganic nutrient nitrogen for anaerobic microorganisms.

6. A chemical composition in accordance with claim 1, further comprising a source of complex, biologically hydrolyzable nutrient phosphorus of from about 0.25% to 15% by weight percent of the composition, said source of complex, biologically hydrolyzable nutrient phosphorus selected from the group consisting of ringed metaphosphates, linear polyphosphates and combinations thereof.

7. A chemical composition in accordance with claim 1, further comprising a binding agent of from about 0.05% to 7% by weight percent of the composition.

8. A solid-chemical composition which provides for extraction and absorption of hydrophobic chemical contaminants and further promotes biodegradation of said contaminants comprising:
   a. One or more plant fiber-containing materials from plant families selected from the group consisting of Leguminosae and Phaeophyta, comprising from about 20% to 97% by weight percent of the composition;
   b. one or more plant fiber-containing materials from plant families selected from the group consisting of Gossypium and Cannabacea, comprising from about 3% to 80% by weight percent of the composition; and
   c. a source of microorganisms which produce plant-fiber and organic-substrate degrading enzymes, from about 0.0001% to 3% by weight percent of the composition.

9. A chemical composition in accordance with claim 8, wherein said source of microorganisms is comprised of forms selected from the group consisting of dehydrated cultures, freeze-dried cultures, encapsulated culture, spores and combinations thereof.

10. A chemical composition in accordance with claim 8, which further includes an inorganic source of microbial electron acceptors and an ammonium-free source of inorganic nutrient nitrogen for anaerobic microorganisms.

11. A chemical composition in accordance with claim 8, further comprising a source of complex, biologically hydrolyzable nutrient phosphorus of from about 0.25% to 15% by weight percent of the composition, said source of complex, biologically hydrolyzable nutrient phosphorus selected from the group consisting of ringed metaphosphates, linear polyphosphates and combinations thereof.

12. A chemical composition in accordance with claim 8, further comprising a binding agent of from about 0.1% to 7% by weight percent of the composition.

13. A chemical composition in accordance with claims 3 or 8, wherein said source of microorganisms which produce plant-fiber degrading enzymes and organic-substrate degrading enzymes produce enzymes selected from the group consisting of cellulases, amylases, glucanases, hemicellulases, proteases, chitinases, lipases and combinations thereof.

14. A chemical composition in accordance with claims 3 or 8, wherein said source of microorganisms which produce plant-fiber and organic substrate degrading enzymes are resistant to or tolerant of mechanical abrasion, compaction, heat, steam, freezing temperatures and pressure.

15. A chemical composition in accordance with claims 4 or 9, wherein said forms of said microorganisms which produce plant-fiber and organic-substrate degrading enzymes provide resistance to or tolerance of mechanical abrasion, compaction, heat, steam, freezing temperatures and pressure.

16. A chemical composition in accordance with claims 5 or 10, wherein said inorganic source of microbial electron acceptors and an ammonium-free source of inorganic nutrient nitrogen for anaerobic microorganisms is selected from the group consisting of sodium nitrate, sodium-potassium nitrate, potassium nitrate, ferric nitrate, manganese nitrate, manganese nitrate tetrahydrate, manganese nitrate hexahydrate and combinations thereof.

17. A chemical composition in accordance with claims 6 or 11, wherein said source of complex, biologically hydrolyzable nutrient phosphorus is selected from the group consisting of sodium hexametaphosphate, sodium trimetaphosphate, sodium tripolyphosphate, sodium-potassium tripolyphosphate, potassium tripolyphosphate, tetrasodium pyrophosphate and combinations thereof.

18. A chemical composition in accordance with claims 1 or 8, further comprising a source of chelating agents of from about 0.01% to 5% by weight percent of the composition, are said chelating agents are selected from the group consisting of citric acid humic acid, fulvic acid, sodium citrate, nitrilotriacetic acid (NTA), ethylenediaminetetraacetic acid (EDTA) and combinations thereof.

19. A chemical composition in accordance with claims 7 or 12, wherein said binding agent is selected from the group consisting of pre-gelled starch, starch, liquid molasses, dried molasses, granulated sugar, corn syrup, dried corn syrup, guar gum, xanthum gum, locust bean gum, barley malt extract, vegetable oils, vegetable fats, animal oils, animal fats, animal lards, glycerin, gelatine, bentonite, montmorillonite, kaolinite, and calcium carbonate.

20. A chemical composition in accordance with claims 1, 2, 3, 8, 13, 4, 9, 14, 15, 5, 6, 10, 11, 16, 17, 18, 7, 12, 19, wherein said composition is prepared in forms selected from the group consisting of granules, briquettes, pellets, blocks, tablets, capsules and combinations thereof.

21. A method for the bioremediation of chemical contaminants in environmental media, wherein said chemical composition in accordance with claims 1, 2, 3, 8, 13, 4, 8, 14, 15, 5, 6, 10, 11, 16, 17, 18, 7, 12, 19 is applied to said environmental media in an amount of about 0.1 g to 1000 g of said chemical composition per Kg of said environmental media.

* * * * *